(12) United States Patent
Suehling

(10) Patent No.: US 11,854,705 B2
(45) Date of Patent: Dec. 26, 2023

(54) METHOD AND SYSTEM FOR SUPPORTING CLINICAL DECISIONS

(71) Applicant: Siemens Healthcare GmbH, Erlangen (DE)

(72) Inventor: Michael Suehling, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 148 days.

(21) Appl. No.: 16/150,407

(22) Filed: Oct. 3, 2018

(65) Prior Publication Data
US 2019/0108917 A1 Apr. 11, 2019

(30) Foreign Application Priority Data
Oct. 10, 2017 (EP) .................................... 17195681

(51) Int. Cl.
*G16H 50/70* (2018.01)
*G16H 10/60* (2018.01)
(Continued)

(52) U.S. Cl.
CPC ............. *G16H 50/70* (2018.01); *G16H 10/60* (2018.01); *G16H 30/40* (2018.01); *G16H 50/20* (2018.01);
(Continued)

(58) Field of Classification Search
CPC ........ G16H 10/60; G16H 50/70; G16H 30/40; G16H 50/20; G16H 15/00; G16H 10/20
See application file for complete search history.

(56) References Cited

U.S. PATENT DOCUMENTS

| | | | |
|---|---|---|---|
| 8,823,928 B2* | 9/2014 | Herzog | G01J 3/36 356/213 |
| 2005/0049497 A1* | 3/2005 | Krishnan | G16H 50/20 600/437 |

(Continued)

FOREIGN PATENT DOCUMENTS

| | | |
|---|---|---|
| EP | 2562690 A2 | 2/2013 |
| WO | WO 2013179216 A2 | 12/2013 |

OTHER PUBLICATIONS

Mesbah, et.al., "Hashing Forests for Morphological Search and Retrieval in Neuroscientific Image Databases", MICCAI (2015) Part II, LNCS 9350, pp. 135-143.* Mesbah, et al. "Hashing Forests for Morphological Search and Retrieval in Neuroscientific Image Databases". MICCAI (2015), Part II, LNCS, 9350, pp. 135-143 (Year: 2015).*

(Continued)

*Primary Examiner* — Robert A Sorey
*Assistant Examiner* — Kristine K Rapillo
(74) *Attorney, Agent, or Firm* — Harness, Dickey & Pierce, P.L.C.

(57) ABSTRACT

A method is for supporting clinical decisions for a diagnosis or therapy of a patient using a medical imaging system. An embodiment of the method includes receiving a procedure order; based on the received procedure order, automatically identifying a clinical context of the ordered procedure; generating preliminary imaging data of at least a part of the patients anatomy; generating feature extraction data based on the identified clinical context and on the preliminary imaging data; extracting at least one clinical context specific feature using the generated feature extraction data; annotating the at least one extracted clinical context specific feature to obtain at least one annotated extracted feature; and selecting, for the identified clinical context, a similar case data set from a reference database of case data sets based on the at least one annotated extracted feature.

26 Claims, 2 Drawing Sheets

(51) Int. Cl.
*G16H 50/20* (2018.01)
*G16H 30/40* (2018.01)
*G16H 15/00* (2018.01)
*G16H 10/20* (2018.01)
*G16H 30/20* (2018.01)

(52) U.S. Cl.
CPC ............. *G16H 10/20* (2018.01); *G16H 15/00* (2018.01); *G16H 30/20* (2018.01)

(56) References Cited

U.S. PATENT DOCUMENTS

| | | | |
|---|---|---|---|
| 2014/0089000 A1 | 3/2014 | Takata et al. | |
| 2014/0350953 A1* | 11/2014 | Liu | A61M 5/007 705/2 |
| 2015/0161329 A1 | 6/2015 | Mabotuwana et al. | |
| 2015/0347682 A1* | 12/2015 | Chen | G16H 50/20 705/2 |
| 2016/0128649 A1* | 5/2016 | Miyazawa | A61B 6/545 378/21 |
| 2017/0323442 A1 | 11/2017 | Suehling | |
| 2018/0068083 A1* | 3/2018 | Cohen | G16B 50/30 |
| 2018/0173852 A1* | 6/2018 | Lou | G16H 40/40 |
| 2018/0341747 A1* | 11/2018 | Bernard | G06N 3/04 |

OTHER PUBLICATIONS

"Hamming distance": in: Wikipedia; Version of: Feb. 20, 2016; https://en.wikipedia.org/wiki/Hamming_distance.

"Relative neighborhood graph"; in: Wikipedia; Version of: Mar. 17, 2013; https://en.wikipedia.org/wiki/Relative_neighborhood_graph.

"Hash Function", in: Wikipedia, Version of: Mar. 4, 2016; http://en.wikipedia.org/wiki/Hash_function.

Lin, Kevin et.al.: "Deep Learning of Binary Hash Codes for Fast Image Retrieval"; in: IEEE Conference on Computer Vision and Pattern Recognition Workshops (CVPRW); 2015; ISSN 2160-7516.

Mesbah, Sepideh et. al.: "Hashing Forests for Morphological Search and Retrieval in Neuroscientific Image Databases"; in: International Conference on Medical Image Computing and Computer-Assisted Interventions (MICCAI); Lecture Notes in Computer Science; vol. 9350; pp. 135-143; 2015; ISBN 978-3-319-24570-6.

Extended European Search Report #17195681.6 dated Apr. 10, 2018.

Jiang, Menglin et al: "Joint Kemel-Based Supervised Hashing for Scalable Histopathological Image Analysis"; Oct. 5, 2015; Advances in Biometrics: International Conference; ICB 2007; Seoul, Korea; Aug. 27-29, 2007; Proceedings; [Lecture Notes in Computer Science; Lect.Notes Computer]; Springer; Berlin, Heidelberg; pp. 366-373; XP047321442; ISBN: 978-3-540-74549-5; 2015.

* cited by examiner

METHOD AND SYSTEM FOR SUPPORTING CLINICAL DECISIONS

PRIORITY STATEMENT

The present application hereby claims priority under 35 U.S.C. § 119 to European patent application number EP17195681.6 filed Oct. 10, 2017, the entire contents of which are hereby incorporated herein by reference.

FIELD

Embodiments of the invention generally relate to a method and a system for supporting clinical decisions. Embodiments further generally relates to a computer readable medium and a computer program product for supporting clinical decisions.

BACKGROUND

Similar case retrieval is a powerful approach for clinical decision support. The basic principle is that for a given case with unknown diagnosis or therapy decision, the Clinical Decision Support System (CDS) should provide a set of very similar cases with known diagnosis, course of disease, or therapy outcome. The similar cases are retrieved from a given patient population data pool based on features extracted from the patients phenotype, in particular, imaging features. The similar cases then provide evidence-based decision support on how to diagnose, treat, or manage the patient. Based on the extracted features, the similar cases may be grouped into homogenous sub-groups that may correspond e.g. to patients that respond well to certain tailored therapies.

Similar image retrieval is described e.g. in Kevin Lin, Huei-Fang Yang, Jen-Hao Hsiao, Chu-Song Chen, "Deep Learning of Binary Hash Codes for Fast Image Retrieval", IEEE Conference on Computer Vision and Pattern Recognition Workshops (CVPRW), 2015, DeepVision workshop. Use of hashing forests for image retrieval in neuroscientific image databases is described e.g. in S. Conjeti, S. Mesbah, A. Kumaraswamy, P. Rautenberg, N. Navab, A. Katouzian, "Hashing forests for morphological search and retrieval in neuroscientific image databases", Proceedings of the 18th International Conference on Medical Image Computing and Computer Assisted Interventions, (MICCAI), Munich, Germany, October 2015.

With the advent of big data infrastructures (e.g. cloud computing) this approach becomes even more applicable as the similar case retrieval can be based on a very large number of patients that may even be shared across institutions.

Features which are contained in medical imaging data, for example computed tomography (CT) imaging data, play a core role for characterizing a case. A key limitation of current approaches is that image features are computed from images primarily generated for reading by the radiologist. For example, CT data that is sent to a Picture Archiving and Communication System (PACS) for reading exhibit thick slices or smooth reconstruction kernels. Feature extraction from these image data optimized for fast network transmission and human reading is often not suited for e.g. the extraction of detailed texture features.

Traditionally, features are extracted from imaging data that has been generated and optimized for human image reading and not for computer-based analysis. In addition, data sent to PACS or reading workstations (also referred to as reading clients) has limited resolution to reduce the image data size for faster network transmission and reduction of PACS storage space.

SUMMARY

The inventors have discovered that features extracted from such data are typically suboptimal or even not usable for feature extraction to characterize a case (e.g. the texture of a lesion or the lung parenchyma). Consequently, the retrieval of similar cases is only very approximate and coarse, providing very limited decision support.

In embodiments of the invention, disclosed are a method and system for supporting clinical decisions for a diagnosis or therapy of a patient using a medical imaging system based on similar image recognition and/or retrieval.

At least one embodiment of the invention provides a method for supporting clinical decisions for a diagnosis or therapy of a patient using a medical imaging system comprising:
  receiving a procedure order;
  based on the received procedure order, automatically identifying a clinical context of the ordered procedure;
  generating preliminary imaging data of at least a part of the patients anatomy;
  generating feature extraction data based on the identified clinical context and on the preliminary imaging data;
  extracting at least one clinical context specific feature using the generated feature extraction data;
  annotating the at least one extracted clinical context specific feature to obtain at least one annotated extracted feature; and
  for the identified clinical context, selecting a similar case data set from a reference database of case data sets based on the at least one annotated extracted feature.

At least one embodiment of the invention further provides a system for supporting clinical decisions for a diagnosis or therapy of a patient using a medical imaging system comprising the steps particular according to one of the preceding claims, wherein the system comprises:
  a receiving unit adapted to receive a procedure order;
  an identifying unit adapted to automatically identify a clinical context of the ordered procedure, based on the received procedure order;
  an preliminary imaging data generating unit adapted to generate preliminary imaging data of at least a part of the patient's anatomy;
  a feature extraction data generating unit adapted to generate feature extraction data based on the identified clinical context and on the preliminary imaging data;
  an extraction unit adapted to extract at least one clinical context specific feature using the generated feature extraction data;
  an annotating unit adapted to annotate the at least one extracted clinical context specific feature to obtain at least one annotated extracted feature; and
  a selection unit adapted to select, for the identified clinical context, a similar case data set from a reference database of case data sets based on the at least one annotated extracted feature.

At least one embodiment of the invention further provides a system for supporting clinical decisions for a diagnosis or therapy of a patient using a medical imaging system, the system comprising:
  a memory storing program computer-readable instructions; and one or more processors configured to execute the instructions such that the one or more processors are configured to, receive a procedure order, automatically identify, based on the procedure order received, a clinical context of the procedure order;

generate preliminary imaging data of at least a part of an anatomy of the patient, generate feature extraction data based on the clinical context identified and on the preliminary imaging data generated, extract at least one clinical context specific feature using the feature extraction data generated, annotate the at least one clinical context specific feature extracted, to obtain at least one annotated extracted feature, and select, for the clinical context identified, a similar case data set from a reference database of case data sets, based on the at least one annotated extracted feature.

An embodiment of the invention further provides a computer-readable medium on which are stored program elements that can be read and executed by a computer unit in order to perform steps of the method according to any of the embodiments of the invention when the program elements are executed by the computer unit.

An embodiment of the invention further provides a computer program product with program elements that can be read and executed by a computer unit in order to perform steps of the method according to any of the embodiments of invention when the program elements are executed by the computer unit.

DETAILED DESCRIPTION OF THE EXAMPLE EMBODIMENTS

Figure 1:
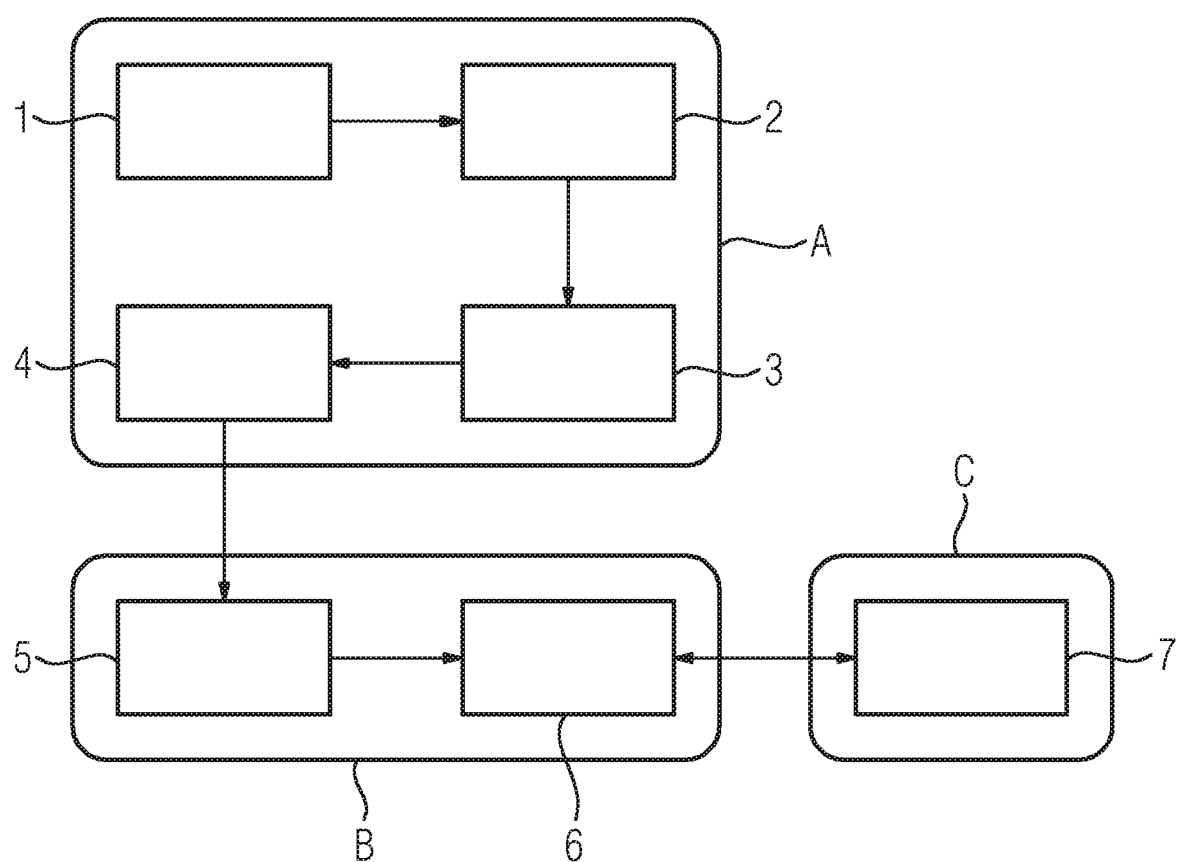
FIG. 1 shows a schematic representation of the method of an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Accordingly, at least one embodiment of the invention provides a method for supporting clinical decisions for a diagnosis or therapy of a patient using a medical imaging system comprising:

a. receiving a procedure order;
b. based on the received procedure order, automatically identifying a clinical context of the ordered procedure;
c. generating preliminary imaging data of at least a part of the patients anatomy;
d. generating feature extraction data based on the identified clinical context and on the preliminary imaging data;
e. extracting at least one clinical context specific feature using the generated feature extraction data;
f. annotating the at least one extracted clinical context specific feature to obtain at least one annotated extracted feature; and
g. for the identified clinical context, selecting a similar case data set from a reference database of case data sets based on the at least one annotated extracted feature.

A procedure order can be in the form of a modality worklist and/or can include e.g. information about an admitting diagnosis. The items in the worklist can include relevant details about the subject of the procedure (patient ID, name, sex, and age), the type of procedure (equipment type, procedure description, procedure code) and the procedure order (referring physician, accession number, reason for exam). A medical imaging system or device, such as a CT scanner, can e.g. query a database or information system, such as a Radiology Information System (RIS), to get this information which can e.g. then be presented to the system operator and can e.g. be used by the medical imaging system to add details in the image metadata. A particular example of such a modality worklist would be a DICOM modality worklist in the DICOM standard. In other words, the specific clinical context for which an imaging exam, e.g. a CT exam is ordered can be defined from the modality worklist information or by manual input at the imaging device, e.g. at the CT scanner.

Preliminary imaging data may comprise e.g. raw data or additional reconstructed image data which has been reconstructed not for the primary purpose of viewing, but for extracting features, e.g. thin slice data, with reconstruction parameters optimized for the given clinical context are generated to extract features from. In case the preliminary imaging data comprises additional reconstructed image data, the additional data generated is intended for feature extraction, not for human reading. Based on the thus generated data (i.e. the feature extraction data) features specific to the clinical context are extracted. In some cases it may be preferred to use imaging raw data for as basis for the generation of feature extraction data, in other cases it may be preferred to use additional reconstructed image data.

The preliminary imaging data may comprise or consist of imaging raw data. Imaging raw data comprises e.g. projection data or sinogram data of CT scanners.

The extracted features are then annotated. This serves to compress the extracted features by representing them in compact form. As an example, annotations in the form of hash codes may be used.

The annotated features are stored along with the image data intended for human reading, which may e.g. be sent to a PACS or a reading client.

Then, based on the annotated features, a similar case data set is selected from a reference database and thus efficiently identified. As an example, the reference database comprises a connected hash code data base containing features of an already annotated collection of image data of a patient population.

The identified similar case data set may contain further information, e.g. identification of one or more similar patients, clinical data, a link or reference to image data sets of said one or more similar patients or report data as would be commonly stored/provided in a PACS or RIS.

The information that is available for the identified similar case set (or for a plurality of similar case sets) may then be used as guidance or information resource for the operating personnel, including the examining physician, for the further diagnosis and treatment of the patient, e.g. as guidance to order further diagnostic procedures, as guidance for therapy decisions, and as guidance for performing further analysis of the patients image data, e.g. by using image analysis applications. This information may further be used to adapt image reconstruction parameters for further image reconstructions from the imaging raw data or to adapt scanning parameters in case further scans of the same patient are ordered on the same imaging modality or on a different imaging modality.

The medical imaging system can be any medical imaging system used for generating imaging data for medical (e.g. diagnostic or therapeutic) purposes, e.g. CT scanner, a magnetic resonance imaging scanner (MRI scanner), an ultrasound scanner a PET/CT scanner, PET/MRI scanner or the like.

According to an embodiment of the invention, it is provided that the procedure order comprises at least one information element of at least one of a request for at least one specific scan parameter of the medical imaging device, a request for a specific scan protocol for the medical imaging device, a request for information on a specific region of a patient's anatomy, a request for organ specific information, a request for disease specific information, clinical data, and disease classification data; and wherein the at least one information element is automatically extracted from the procedure order or from a prior procedure report relating to the patient, wherein a prior procedure report may be obtained from a radiology information system (RIS) or hospital information system (HIS).

According to an embodiment of the invention, it is provided that step c. further comprises the step of reconstructing image data from the preliminary imaging data for outputting to a viewing device or data storage device.

According to an embodiment of the invention, it is provided that the feature extraction data comprises at least one data extraction element from the group of at least one of an image reconstruction parameter, a time dependent data acquisition parameter, and an image scan parameter.

According to an embodiment of the invention, it is provided that the at least one clinical context specific feature is a feature from the group of texture feature, material specific feature, a morphological feature, and a contrast feature.

According to an embodiment of the invention, it is provided that in step f. annotating comprises applying a hash function to the at least one extracted clinical context specific feature. Applying a hash function allows the assignment of a hash code to the extracted feature.

According to an embodiment of the invention, it is provided that the at least one clinical context specific feature or the at least one annotated extracted feature is added to an image data set at least a part of the patients anatomy in the form of an image attribute or a separate report associated with the image data set.

According to an embodiment of the invention, it is provided that the similar case data set comprises a determined similarity to a case data set of the patient.

According to an embodiment of the invention, it is provided that the similarity is determined based on a member of at least one of determination of a Hamming Distance, use of a Random Forest Function, use of a Deep Learning Function, use of a list of reference database case data sets ranked according to similarity, and use of a neighborhood graph indicating clusters of similar reference database case data sets.

An embodiment of the invention further provides a system for supporting clinical decisions for a diagnosis or therapy of a patient using a medical imaging system comprising the steps particular according to one of the preceding claims, wherein the system comprises:

a. a receiving unit adapted to receive a procedure order;
b. an identifying unit adapted to automatically identify a clinical context of the ordered procedure, based on the received procedure order;
c. an preliminary imaging data generating unit adapted to generate preliminary imaging data of at least a part of the patient's anatomy;
d. a feature extraction data generating unit adapted to generate feature extraction data based on the identified clinical context and on the preliminary imaging data;
e. an extraction unit adapted to extract at least one clinical context specific feature using the generated feature extraction data;
f. an annotating unit adapted to annotate the at least one extracted clinical context specific feature to obtain at least one annotated extracted feature;

g. a selection unit adapted to select, for the identified clinical context, a similar case data set from a reference database of case data sets based on the at least one annotated extracted feature.

The system according to an embodiment of the present invention or specific components of the system, in particular the components a, b, and c, may be provided in a medical imaging system such as a CT scanner.

According to another embodiment of the present invention, it is provided that further components of the system, in particular the reference database is part of a network, wherein preferably the database and a medical imaging system are in communication with each other. By using a common network, it is advantageously possible to establish a central update as well as collecting case data sets from different local medical imaging systems. Thus, the quality of selecting a similar case data set is further improved. Preferably, there is an interface for communicating between the local medical imaging system and the network.

It is also thinkable that some or all of the components d, e, f, or g are integrated into the medical imaging system, wherein the selection unit is configured for accessing the database, or that that some or all of the components d, e, f, or g are integrated in the database. In the case that some or all of the components d, e, f, or g are integrated in the database, one of the preliminary imaging data, the feature extraction data, the clinical context specific feature or the annotated extracted feature, respectively, is transferred to the database for completing the required steps for selecting a similar case data set. Such a networked solution could be implemented via an internet platform and/or in a cloud-based computing system.

An embodiment of the invention further provides a computer-readable medium on which are stored program elements that can be read and executed by a computer unit in order to perform steps of the method according to any of the embodiments of the invention when the program elements are executed by the computer unit.

An embodiment of the invention further provides a computer program product with program elements that can be read and executed by a computer unit in order to perform steps of the method according to any of the embodiments of invention when the program elements are executed by the computer unit.

In FIG. 1, a schematic representation of the method of an embodiment of the invention is shown. In a first step (1) a procedure order is received. The procedure order can be received by manual input from operating personnel or by data transfer of a respective request for a procedure.

This procedure order contains clinical context specific information as will be explained in more detail below. This allows to automatically identify a clinical context of the ordered procedure (2). Imaging raw data of at least a part of the patients anatomy is then generated (3).

The step of generating preliminary imaging data (3) may occur—as shown in FIG. 1 subsequently to the step of automatically identifying a clinical context (2). Alternatively, the step of generating preliminary imaging data (3) may also occur prior to or in parallel to the step of automatically identifying a clinical context (2).

Then, feature extraction data based on the identified clinical context and on the preliminary imaging data is then generated (4). The feature extraction data is used to extract clinical context specific features (5) to obtain at least one extracted clinical context specific feature and the extracted features are annotated (6) to obtain at least one annotated extracted feature.

For the identified clinical context, one or more similar case data sets from a reference database of case data sets based on annotated extracted features is then selected (7).

Making the selection of the at least one similar case data sets based on annotated extracted features rather than based on the extracted clinical context specific features, enables a quick and systematic selection. Using the annotated feature has the effect of compressing the data volume of extracted features greatly, because now only the respective annotation can be used for the identification of similar case data sets.

The steps (1), (2), (3), and (4), can take place at a medical imaging system (A) or be implemented in the controller of a medical imaging system (A). Processing the preliminary imaging data locally at the medical imaging system to the point where feature extraction data is generated (4) avoids the need for transferring the preliminary imaging data to a further data processing location.

The steps (5) and (6) can take place at the medical imaging system (A) or at a separate reading client (B) which is typically used to receive and analyse imaging data from the medical imaging system (A).

The step of selection of a similar case data set (7), relies on the selection from a reference database which can be provided in an external electronic archive (C).

According to alternative embodiments of the invention it is also provided, that steps (5), (6), and (7), can take place at the site of the external electronic archive or be implemented in a computing cloud.

Figure 2:
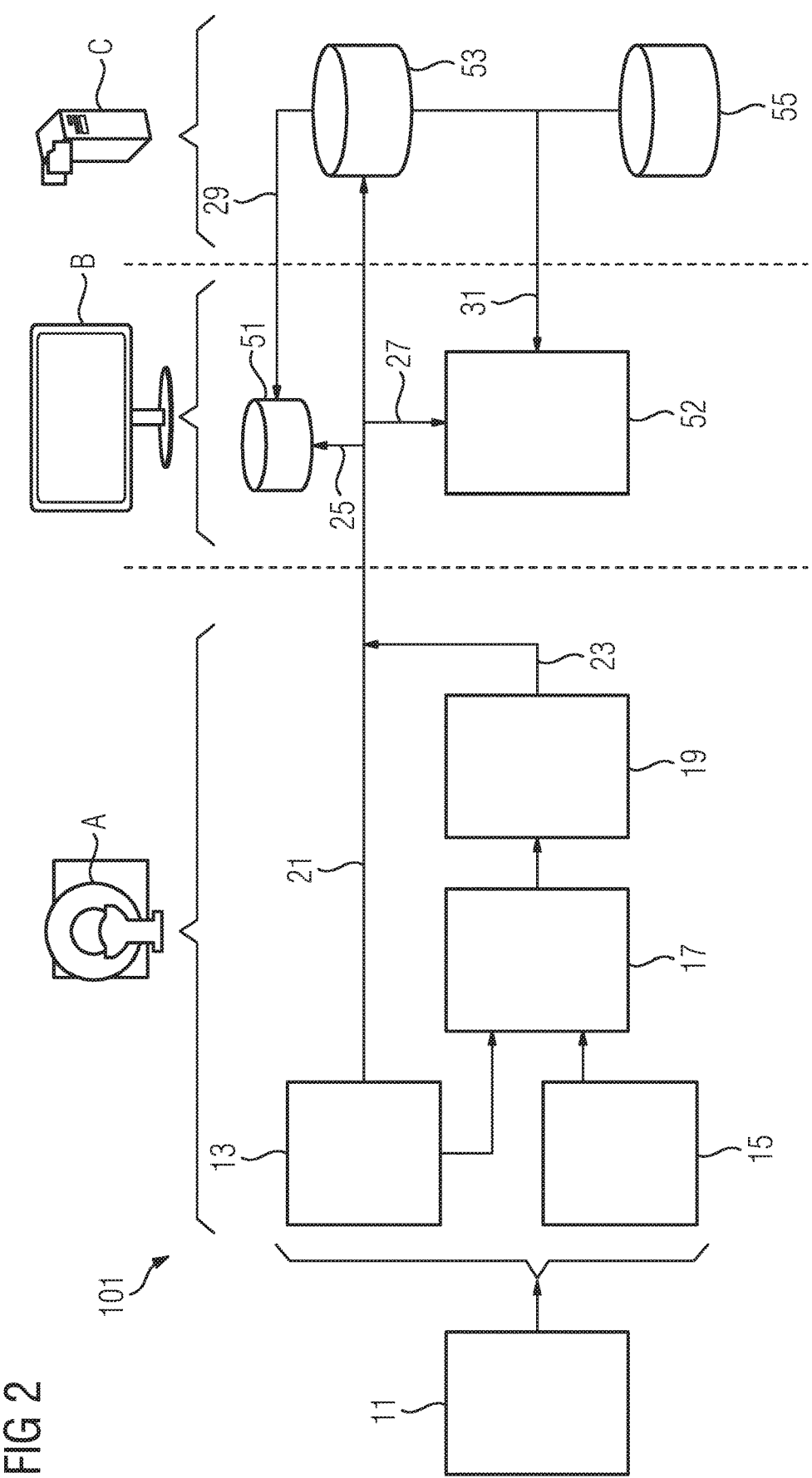
FIG. 2 shows an overview schematically illustrating an example embodiment of the method and system of the invention.

In FIG. 2, an overview schematically illustrating an example embodiment of the method and system (101) of the invention is shown. In this example embodiment, some steps of the method and some components of the system (101) are implemented in a medical imaging system (A), for example, a CT scanner, in a reading client (B) and an archive (C).

First, the medical imaging system (A) receives a procedure order (11), e.g. in the form of a modality worklist. Receiving the procedure order can be implemented via a receiving unit, for example via an input device of the medical imaging system (e.g. a control panel, touch display or the like), or via a data receiving interface. The next step of the method comprises automatically defining the clinical context of the ordered scan in an identifying unit (not shown, it can be e.g. provided in the control unit of the medical imaging system). One way to do this is to use e.g. the "admitting diagnosis" from the procedure order. Commonly a diagnostic scan on a medical imaging system is ordered in the context of an admitting diagnosis, i.e. it is requested in order to confirm, rule out or provide further information with regard to a suspected diagnosis of an admitted patient.

For instance, the admitting diagnosis could be "Chronic obstructive pulmonary disease (COPD)" or "angina pectoris". An admitting diagnosis may be associated with a standardized code, such as an ICD-10 code or a similar standardized disease code or diagnosis code. The ICD-10 list of codes is a medical classification list provided by the World Health Organization (WHO). It contains codes for diseases, signs and symptoms, abnormal findings, complaints, social circumstances, and external causes of injury or diseases. For instance, the admitting diagnosis could be ICD-10-CM diagnosis code J44.1: "Chronic obstructive pulmonary disease (COPD) with (acute) exacerbation" or code I25.11, "Atherosclerotic heart disease of native coronary artery with angina pectoris".

Additional information for clinical context identification could be extracted from other parameters of the modality worklist and from prior diagnostic or procedure reports that can be automatically fetched from the archive (C), e.g. from a RIS (55) or HIS (55) (Radiology Information system or Hospital Information System, respectively) upon the reception of the procedure order at the medical imaging system. This additional information may include information on selected scan parameters, information on previous examinations or scans of the same patient or the like. The clinical context may also be supplied, augmented or edited by input from the personnel operating the medical imaging system (A).

Thus, the procedure order inherently comprises information which provides a basis for clinical context. This information can include as a non-limiting list of examples:
- the specific region of a patient's anatomy to be scanned (e.g. "thorax"),
- scan parameters (e.g. "dual energy" or "contrast enhanced"),
- previous examination information (e.g. if a patient is monitored regularly in the same diagnostic context or scenario)
- an admitting diagnosis (e.g. "angina pectoris" or "COPD"),
- an admitting diagnosis including a standardized code (e.g. ICD-10 code "I25.11, Atherosclerotic heart disease of native coronary artery with angina pectoris" or code J44.1: "Chronic obstructive pulmonary disease (COPD) with (acute) exacerbation"),
- clinical context information added by operating personnel.

Thereby, the system can automatically identify a clinical context of the ordered procedure based on the received procedure order. The more information is available, the more precisely the clinical context can be defined, but even a small amount of information, e.g. scanning region and scanning parameters can reveal a great deal about the clinical context.

After the procedure order has been received, the patient is scanned the medical imaging system and preliminary imaging data generated by a preliminary imaging data generating unit (not shown), which may e.g. comprise the medical imaging systems detector system and accompanying signal processing system.

Optionally, and preferably in parallel to operating the further steps of the inventive method, images may be reconstructed (13) for outputting to a viewing device or data storage device (53) and may be generated for example in DICOM format (21) and sent to a PACS (53) in the archive (C).

According to the method of an embodiment of the invention, dedicated data is generated for feature extraction by a feature extraction data unit (15). This feature extraction data is not necessarily sent to the PACS or a reading client and may be stored at the medical imaging system. It is only needed temporarily and thus may be stored only for a temporary time span. This feature extraction data can comprise the raw data and/or some additional reconstructed image data which has been reconstructed not for the primary purpose of viewing, but for extracting features. Thus the feature extraction data can be provided very quickly, as it is only required to perform a partial reconstruction (if at all) and not a full reconstruction of image data sets for viewing.

Dedicated data for feature extraction ("feature extraction data") can include as a non-limiting list of examples:
- Tailored iterative reconstruction settings: The statistical weighting of the raw data and/or regularization in the image domain may be tuned towards specific features to be extracted. The clinical context serves as prior knowledge for the iterative reconstruction: For instance, for the identification of lung lobe boundaries within the clinical context "COPD", edges in the images may be enhanced significantly (at the price of an increased overall noise level). In another example, for clinical contexts related to vascular or airway reading, tubular-like structures can be enhanced during iterative reconstruction.
- For the clinical context of coronary artery disease, additional heart phases and reconstruction parameterizations may be generated (in the case of ECG-gated acquisitions) to e.g. improve coronary stenosis detection and characterization.
- For the clinical context of lung cancer screening, additional thin slice or in-plane high resolution data may be reconstructed for e.g. texture analysis of lung nodules. Such additional, dedicated data can also be generated locally around a structure of interest relevant for the clinical context. For instance, for lesions automatically detected in a first step, additional reconstructions can be restricted to the Field of View (FoV) of the structure of interest.
- Additional reconstructions with the same parameter settings as used for a prior scan of the given case ensure compatibility and comparability between follow-up data.

In a next step, a feature extraction (17) is performed by a extraction unit to obtain clinical context specific features. For the given clinical context dedicated, context-specific features are extracted from feature extraction data. Features can include as a non-limiting list of examples:
- Texture features for the analysis of lung emphysema in case of the COPD clinical context.
- Features dedicated for coronary lesion characterization (e.g. Dual Energy ratios within coronary arteries) in the case of a Coronary Artery Disease clinical context.
- Features can also contain non-image information such as medical history data (prior medical conditions, drug allergies, medications, etc), clinical data or patient data (patient size, weight, age, sex, results of in-vitro diagnostic tests, etc.).

In a next step, the extracted features are annotated (19) by an annotating unit. As a result the data related to the features can be greatly compressed, because the feature can be represented by its annotation (i.e. "the annotated extracted feature"). For annotating the extracted features, it is possible to use standardized codes.

One approach is to approximate the features by so-called hash codes using a hash function. A hash function is any function that can be used to map data of arbitrary size to data of fixed size. The values returned by a hash function are called hash values or hash codes (also referred simply as "hashes"). One use is a data structure called a hash table, widely used in computer software for rapid data lookup. Hash functions accelerate table or database lookup by detecting duplicated records in a large file. The use of hash codes has two advantages:
- The hash codes provide a very compact approximation of the actual image features reducing the data size of the image feature information to be stored along with the DICOM data.
- Hash codes provide a very efficient vehicle to compare huge amounts of data with respect to similarity (e.g. by using the so-called Hamming distance).

State-of-the art hashing functions such as Random Forests or Deep Learning may also be employed for this purpose. The hashing function is used to generate compact, similarity preserving and easy to compute representations. For example, similar cases will be encoded with same or similar hash codes.

Feature annotation or feature compression may also be realized by ways other than hash codes.

The annotations (for example hash codes) may be added (23) to the DICOM image data (21) intended for human reading in the form of e.g. dedicated DICOM attributes or a separate DICOM Structured Report.

Upon reception of the DICOM image data (21) at the reading Client (B), the hash codes, the corresponding patient identifier (identifier), and the clinical context of the new case are extracted and added (25) to a hash database (51) connected to the reading client (B) (either locally or remotely via a network). This can also be augmented by non-image features for each patient obtained e.g. from medical history data (prior medical conditions, drug allergies, medications, etc), clinical data or patient data (patient size, weight, age, sex, results of in-vitro diagnostic tests, etc.).

In a further step, the annotated extracted features, e.g. the hash codes, are communicated (27) to a selection unit (52). Then, one or more similar cases are selected or identified by the selection unit (52) based on the annotated extracted features.

In the example wherein hash codes are annotated extracted features, the selection can be made by hash code comparison which allows to quickly and efficiently determine a degree of similarity. Given the hash code database of all registered cases/patients and the hash code of the new case for which selection of one or more similar cases is to be performed, the selection unit (52) triggers the retrieval (31) of similar case data sets or retrieval (31) of their respective identifiers for the given clinical context. The identifier is a unique code which allows identification of the similar case data set. The retrieved set of similar case data sets or their respective identifiers is then visualized in an appropriate fashion, e.g. as a list of identifiers ranked according to their degree of similarity or a neighborhood graph indicating clusters of similar patient subsets. The information that is available for the one or more similar case data sets may then be used as guidance for the operating personnel, including the examining physician, as described above The advantage of not precomputing or analyzing a static list of most similar patients directly at the medical imaging system (A) is that the user at the reading client (B) can interactively add or remove features from the overall similarity feature vector. The set of corresponding similar patients can then be updated at the reading client (B).

The visualized similar case data sets or their respective identifiers are associated with links pointing towards the actual data associated with the similar cases respectively. For instance, the links point to the actual DICOM data in the PACS, diagnostic reports in the RIS, or laboratory values in the HIS that may be retrieved from the source database upon a user request (e.g. by click on the associated link) in the similar case identifier visualization.

The retrieval of the actual, detailed data for a similar case is optional. For example, the system may automatically retrieve the full data (images, reports, lab values, etc.) or a configurable subset of the full data for the N most similar cases by default where N is configurable in the system configuration. The reading client (B) and hash code database (51) may be deployed on a cloud infrastructure. By only storing the hash codes, the data to be transferred to the cloud storage is minimized. In addition, not all imaging data needs to be stored in the cloud, reducing storage and bandwidth needs as well as limiting risks related to data privacy.

In case not all cases are sent to a particular reading client with a connected hash code database, hash codes may automatically be polled from the DICOM archive on a regular basis (e.g. during night hours) to update the hash code database connected to the reading client.

Similarity features are computed for a specific clinical context that is identified automatically from the procedure order (modality worklist) or may be manually edited by the personnel operating the medical imaging system. This avoids computational burden and storage resources for unnecessary features. In addition, the approach ensures that features are optimized towards the actual clinical question to be answered and thus provides optimal clinical decision support in the form of best similar cases for the specific clinical context.

For the given clinical context, context-specific additional data/images are generated at the site of the medical imaging system to extract features from. This is preferably done at the medical imaging system where the imaging raw data resides. These context-specific additional reconstructions cannot be generated at a reading workstation as the imaging raw data is not available there. Transferring the preliminary imaging data, in particular in the case of imaging raw data, is problematic in practice as it typically is encompasses a very large data volume.

Embodiments of the invention thus provides a very time and resource efficient way of obtaining similar case data sets for a given patient and procedure order. These similar case data sets may then be used for purposes of clinical decision support.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for supporting clinical decisions for a diagnosis or therapy of a patient using a medical imaging system, the method comprising:
   automatically identifying, based on a procedure order, a clinical context of the procedure order;
   generating preliminary imaging data of at least a part of an anatomy of the patient, the preliminary imaging data including imaging raw data, and the imaging raw data including projection data or sinogram data obtained by a first medical imaging apparatus;
   generating feature extraction data based on the clinical context and the preliminary imaging data including the imaging raw data, the feature extraction data being based on imaging data prior to reconstruction for viewing;
   extracting at least one clinical context specific feature based on the feature extraction data;
   annotating the at least one clinical context specific feature, the annotating including applying a hash function to the at least one clinical context specific feature to obtain at least one hash code;
   selecting, for the clinical context, a similar case data set from a reference database of case data sets, based on the at least one hash code; and
   obtaining at least one of an adapted image reconstruction parameter or an adapted scanning parameter based on information included in the similar case data set, the adapted scanning parameter being a selected parameter value usable for performing a future scan of the patient via a second medical imaging apparatus.

2. The method of claim 1, wherein the procedure order includes at least one information element, the at least one information element including at least one of
   a request for at least one specific scan parameter of the first medical imaging apparatus,
   a request for a specific scan protocol for the first medical imaging apparatus,
   a request for information on a specific region of the anatomy of the patient,
   a request for organ specific information, or
   a request for disease specific information, clinical data, or disease classification data; and
   the at least one information element is automatically extracted from (i) the procedure order or (ii) from a prior procedure report relating to the patient, the prior procedure report from a radiology information system or hospital information system.

3. The method of claim 1, wherein the imaging raw data is imaging raw data prior to, or without, full reconstruction of image data for viewing.

4. The method of claim 1, further comprising:
   reconstructing image data from the preliminary imaging data for output to a viewing device or data storage device.

5. The method of claim 1, wherein the feature extraction data includes at least one of
   an image reconstruction parameter,
   a time dependent data acquisition parameter, or
   an image scan parameter.

6. The method of claim 1, wherein the at least one clinical context specific feature includes at least one of
   a texture feature,
   a material specific feature,
   a morphological feature, or
   a contrast feature.

7. The method of claim 1, wherein
   the at least one clinical context specific feature is added to an image data set, and
   at least the part of the anatomy of the patient is in a form of an image attribute or a separate report associated with the image data set.

8. The method of claim 1, wherein the similar case data set includes a similarity to a case data set of the patient.

9. The method of claim 8, wherein the similarity is determined based on at least one of
   determination of a Hamming Distance,
   use of a Random Forest Function,
   use of a Deep Learning Function,
   use of a list of reference database case data sets ranked according to similarity, or
   use of a neighborhood graph indicating clusters of similar reference database case data sets.

10. A system for supporting clinical decisions for a diagnosis or therapy of a patient using a medical imaging system, the system comprising:
    an identifying unit configured to automatically identify, based on a procedure order, a clinical context of the procedure order;
    a preliminary imaging data generating unit configured to generate preliminary imaging data of at least a part of an anatomy of the patient, the preliminary imaging data including imaging raw data, and the imaging raw data including projection data or sinogram data obtained by a first medical imaging apparatus;
    a feature extraction data unit configured to generate feature extraction data based on the clinical context and the preliminary imaging data including the imaging raw data, the feature extraction data being based on imaging data prior to reconstruction for viewing;
    an extraction unit configured to extract at least one clinical context specific feature using the feature extraction data;
    an annotating unit configured to annotate the at least one clinical context specific feature, the annotation of the at least one clinical context specific feature including applying a hash function to the at least one clinical context specific feature to obtain at least one hash code; and
    a selection unit configured to select, for the clinical context, a similar case data set from a reference database of case data sets, based on the at least one hash code,
    wherein the system is configured to obtain at least one of an adapted image reconstruction parameter or an adapted scanning parameter based on information included in the similar case data set, the adapted scanning parameter being a selected parameter value usable for performing a future scan of the patient via a second medical imaging apparatus.

11. A non-transitory computer-readable medium storing program elements, readable and executable by a computer unit, to cause the computer unit to perform the method of claim 1 when the program elements are executed by the computer unit.

12. A non-transitory computer program product storing program elements, readable and executable by a computer unit, to cause the computer unit to perform the method of claim 1 when the program elements are executed by the computer unit.

13. The method of claim 2, further comprising:
    reconstructing image data from the preliminary imaging data for output to a viewing device or data storage device.

14. The method of claim 4, wherein the feature extraction data includes at least one of
an image reconstruction parameter,
a time dependent data acquisition parameter, or
an image scan parameter.

15. The method of claim 4, wherein the at least one clinical context specific feature includes at least one of
a texture feature,
a material specific feature,
a morphological feature, or
a contrast feature.

16. The system of claim 10, further comprising:
a reconstruction unit configured to reconstruct image data based on the preliminary imaging data, for output to a viewing device or a data storage device.

17. A system for supporting clinical decisions for a diagnosis or therapy of a patient using a medical imaging system, the system including a memory and one or more processors, the memory storing computer-readable instructions, and the one or more processors configured to execute the computer-readable instructions such that the one or more processors are configured to:
automatically identify, based on a procedure order, a clinical context of the procedure order;
generate preliminary imaging data of at least a part of an anatomy of the patient, the preliminary imaging data including imaging raw data, and the imaging raw data including projection data or sinogram data obtained by a first medical imaging apparatus;
generate feature extraction data based on the clinical context and the preliminary imaging data including the imaging raw data, the feature extraction data being based on imaging data prior to reconstruction for viewing;
extract at least one clinical context specific feature using the feature extraction data;
annotate the at least one clinical context specific feature, the annotation of the at least one clinical context specific feature including applying a hash function to the at least one clinical context specific feature to obtain at least one hash code;
select, for the clinical context, a similar case data set from a reference database of case data sets, based on the at least one hash code; and
obtain at least one of an adapted image reconstruction parameter or an adapted scanning parameter based on information included in the similar case data set, the adapted scanning parameter being a selected parameter value usable for performing a future scan of the patient via a second medical imaging apparatus.

18. The system of claim 17, wherein the one or more processors are configured to execute the computer-readable instructions such that the one or more processors are further configured to:
reconstruct image data based on the preliminary imaging data, for output to a viewing device or a data storage device.

19. The method of claim 1, wherein the adapted image reconstruction parameter is adapted for use in reconstructing the imaging raw data.

20. The method of claim 1, wherein the first medical imaging apparatus is the same as the second medical imaging apparatus.

21. The method of claim 1, wherein the adapted scanning parameter is a parameter of the second medical imaging apparatus.

22. The method of claim 1, wherein the adapted scanning parameter is for a dual energy scan or a contrast enhanced scan.

23. The system of claim 10, wherein the first medical imaging apparatus is the same as the second medical imaging apparatus.

24. The system of claim 17, wherein the first medical imaging apparatus is the same as the second medical imaging apparatus.

25. The system of claim 10, wherein the adapted scanning parameter is for a dual energy scan or a contrast enhanced scan.

26. The system of claim 17, wherein the adapted scanning parameter is for a dual energy scan or a contrast enhanced scan.

* * * * *